United States Patent
Meyer

(10) Patent No.: US 6,860,864 B2
(45) Date of Patent: Mar. 1, 2005

(54) D-DAFO (DEROSS-DYNAMIC ANKLE FOOT ORTHOSIS)

(76) Inventor: Grant C. Meyer, 1432 Lakeshore Dr., Muskegon, MI (US) 49441

( * ) Notice: Subject to any disclaimer, the term of this patent is extended or adjusted under 35 U.S.C. 154(b) by 166 days.

(21) Appl. No.: 10/034,658

(22) Filed: Dec. 28, 2001

(65) Prior Publication Data

US 2003/0125653 A1 Jul. 3, 2003

(51) Int. Cl.⁷ .................................................. A61F 5/00
(52) U.S. Cl. .......................................... 602/27; 128/882
(58) Field of Search ................................. 128/882, 845, 128/846; 602/27, 28, 65, 66, 61, 60, 23, 5; 36/54, 68, 99

(56) References Cited

U.S. PATENT DOCUMENTS

| | | | |
|---|---|---|---|
| 970,393 A | * 9/1910 | Raymond | 36/54 |
| 1,275,895 A | * 8/1918 | Fox | 36/54 |
| 2,454,335 A | * 11/1948 | Nichols | 24/713.4 |
| 4,282,659 A | * 8/1981 | Bourque et al. | 36/118.2 |
| 4,351,324 A | * 9/1982 | Bronkhorst | 602/27 |
| 4,454,871 A | 6/1984 | Mann et al. | |
| 4,505,269 A | * 3/1985 | Davies et al. | 602/27 |
| 4,934,355 A | * 6/1990 | Porcelli | 602/16 |
| 4,938,777 A | * 7/1990 | Mason et al. | 623/50 |
| 5,020,523 A | * 6/1991 | Bodine | 602/27 |
| 5,259,834 A | * 11/1993 | Wittmeyer | 602/28 |
| 5,282,483 A | * 2/1994 | Wang | 128/882 |
| 5,370,604 A | * 12/1994 | Bernardoni | 602/27 |
| 5,593,383 A | * 1/1997 | DeToro | 602/27 |
| 5,609,568 A | * 3/1997 | Andrews | 602/28 |
| 5,665,059 A | 9/1997 | Klearman et al. | |
| 5,897,515 A | 4/1999 | Willner et al. | |
| 6,146,349 A | 11/2000 | Rothschild et al. | |
| 6,173,511 B1 | 1/2001 | Perrault | |
| 6,283,932 B1 | * 9/2001 | Munch et al. | 602/23 |

OTHER PUBLICATIONS

US 2001/0042324A1.*

* cited by examiner

Primary Examiner—Nicholas D. Lucchesi
Assistant Examiner—Huong Q. Pham
(74) Attorney, Agent, or Firm—Lance Englund

(57) ABSTRACT

The D-DAFO (DeRoos-Dynamic Ankle Foot Orthosis) invention is a dynamic support system designed to maintain the correct alignment of the bones in the foot and ankle. The D-DAFO's dynamic stability allows the patient's tibia to rotate forward anteriorly and yet supported, while continuously providing the support to hold the patient in sub-talar neutral, and/or improved alignment for function, while simultaneously maintaining tone and extension synergy.

5 Claims, 3 Drawing Sheets

D-DAFO (DEROSS-DYNAMIC ANKLE FOOT ORTHOSIS)

BACKGROUND OF THE INVENTION

1. Field of the Invention

The present invention relates to the DeRoos-Dynamic Ankle Foot Orthosis, designed to maintain the correct alignment of the bones in the foot and ankle to a subtalar neutral position and or improved alignment for function by utilizing a support system of dynamic nature. This dynamic design is of particular benefit benefit to children having spasticity, a condition often scene in cerebral palsy and similar types of medical disorders. The patients are generally confronted with a a muscle imbalance, as their muscles do not work together as normal children's do. Their spasticity makes their muscles overpower other muscles creating unwanted pulls or forces on their joints. This imbalance of muscular pulls, called spastic contractures, creates misalignnient of the involved joints, and if this misalignment is not corrected, it will eventually lead to permanent deformity in the child.

2. Description of the Related Art

The prior art relates generally to conventional static orthosis support systems that are rigid and inflexible while limiting the motion and often restrictive and cumbersome to the patient, just as flexible orthotics do without the biomechanical design to move the patient and restrict unwanted motion. The present D-DAFO invention by contrast is a non restrictive dynamic ankle foot orthosis that allows freedom of motion while maintaining the correct alignment of the bones of the foot and ankle to subtalar neutral position (STN), or improved alignment for function, and restricts the patient from planter flexion and shortening of the heel cord.

U.S. Pat. No. 5,897,515 to Willner and Engdahl describes an ankle foot orthosis comprising a frame extending over the front of the lower leg and a supporting portion of rigid material extending over a narrow part of the front of the lower leg. U.S. Pat. No. 5,665,059 to Klearman, Bronson, and Roth discloses a pivotally adjustable self-supporting ankle/foot orthosis for supporting a patient's ankle in neutral position and a brace extending between the foot section and the calf section for maintaining a relative angle in a fixed position.

U.S. Pat. No. 6,173,511 to Perrault teaches an orthosis for footware with positional self-adjustment formed of a semi-rigid resilient shell and is engaged inside a footware to conformingly fit against the plantar portion of a person's foot, extending from the metatarsal region to the heel portion.

U.S. Pat. No. 4,454,871 to Mann and Hecker describes an anklefoot orthosis positive mold including a pair of longitudinal ribs disposed alongside the lateral and medial surfaces of the lower half of the leg to below the ankle. The orthosis is adapted for securely maintaining the foot and leg of the wearer in a slightly less than 90 deg relationship to one another, the rigidity of the orthosis being enhanced by the longitudinal ribs formed therein.

U.S. Pat No. 6,146,349 to Rothschild and Fox teaches a natural foot orthosis and method of manufacturing the same. The invention describes a copolymer thermoplastic neural foot orthosis for supporting and controlling the movement of a lower extremity and method for manufacturing the same. The orthosis is fabricated by forming a positive mold of the lower extremity, and modifying the positive mold in predetermined locations to accomplish the type of lower extremity control desired.

None of the above recited prior art patents either teach nor disclose the subject invention D-DAFO dynamic ankle foot orthosis and are essentially static rigid and molded support members and do not provide D-DAFO's "dynamic stability" uniqueness to hold the patient in STN (sub-talar) neutral while simultaneously maintaining tone and extension synergy.

SUMMARY OF THE INVENTION

The present DeRoos DAFO invention overcomes the limitations and disadvantages of the prior art static orthosis by correcting misalignment of the bones of the foot and the involved joints dynamically while providing function and comfort to the patient.

The orthosis is and has been utilized in clinical research with children diagnose with cerebral palsy and other neurological pathologies where spasticity is involved, Utilizing conventional orthosis has been difficult with this population because the orthosis were of static force systems. The critical STN may be achieved with these conventional rigid static systems, but wearing compliance, comfort, and tissue breakdown were of constant issue. Few of the patients would comfortably tolerate the objectionable static holding forces.

The results have been remarkable with the dynamic corrected force system with the D-DAFO. The D-DAFO works with circumferential support and dynamic stabilizing forces with the ability to increase or decrease with changes in incremental volume and overriding forces exhibited by the patient's spasticity. The elastic webbing and flexible plastics provide a supporting othosis with a dynamic memory. The dynamics of the orthosis's supporting memory provides the necessary forces to maintain STN (sub-talar neutral) and corrected lower extremity alignment. This dynamic resistance moves with the patient to the point of malalignment limit and then returns the patient to the ideal STN position or the improved alignment for function.

The D-DAFO dynamic support system restricts the patient from planter flexion. Planter flexion is a normal position when the foot is flexed downward. A spastic contracture of the posterior tibial (calf) muscles can hold the foot in that position and produce a shortening of the heel cord. This shortened heel cord can generate additional undesirable positions which can lead to permanent deformity if not treated properly with corrective orthosi, or surgery. Because children are malleable, they can usually be reshaped (molded) even though they may be twisted, turned and out of alignment from spastic contractures. These conditions are much more favorably correctable with the D-DAFO dynamic ankle support system as opposed to the conventional static systems of the prior art!.

Spasticity is commonly described as unwanted motor responses. It occurs because the inhibition normally provided by the brain suppressor areas is not present. Brain lesions disrupt the pathway to the muscles and create hyperactive phasic stretch reflexes, hyperactive tonic reflexes, and clonus, commonly referred to as "tone." The D-DAFO is utilized as a tone reducer and protects the patient from unwanted motion. The orthosis moves with the patient, yet supports and comfortably returns the patient to STN (sub-talar neutral), thus preventing unwanted posture positioning. The D-DAFO is dynamically working to maintain corrected alignment of the foot and ankle and while continuously supporting the STN position. By maintaining this ideal foot and ankle position during the growing years of children, deformities can be prevented and normal morphology and function can be obtained into adulthood. The D-DAFO continuously provides the support to hold the patient in STN yet the freedom to accommodate for high tone and extension synergy unlike conventional orthoses.

BRIFE DESCRIPTION OF THE DRAWINGS

FIG. 1 shows a perspective assembled view of the dynamic foot orthosis including the posterior base shell (7) with upper and lower external flanges (15) & (16), fore-foot metatarsal posting (17), and hind foot posting (18) disposed at the bottom of the posterior base shell (7), tongue (9), Velcro strap (11), elastic Velcro strap (12), and attachmnt fasteners (13) oriented about the vertical axis (4) and the horizontal axis (5).

DETAILED DESCRIPTION OF THE PREFERRED EMBODIMENT

Figure 1:
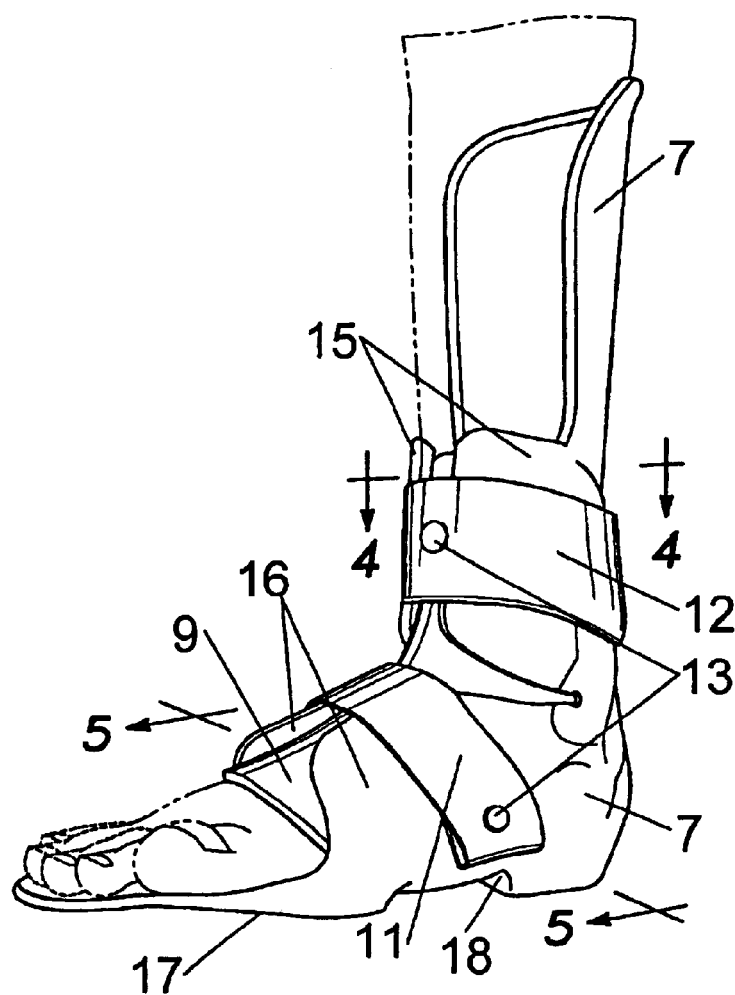
Figure 2:
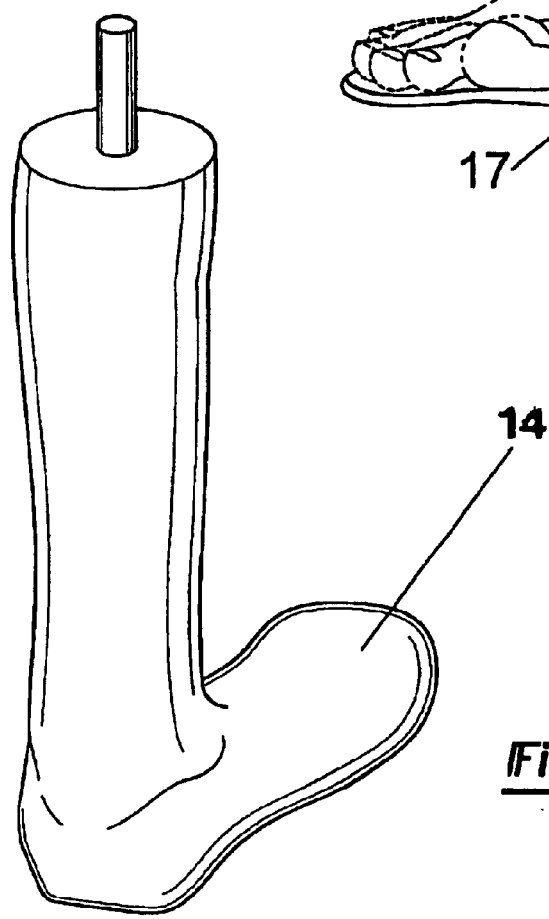
FIG. 2 shows a plaster model of the sject patient's foot (14) that is insertable into the D-DAFO assembly, FIG. 1, for mock-up and sizing.
Figure 3:
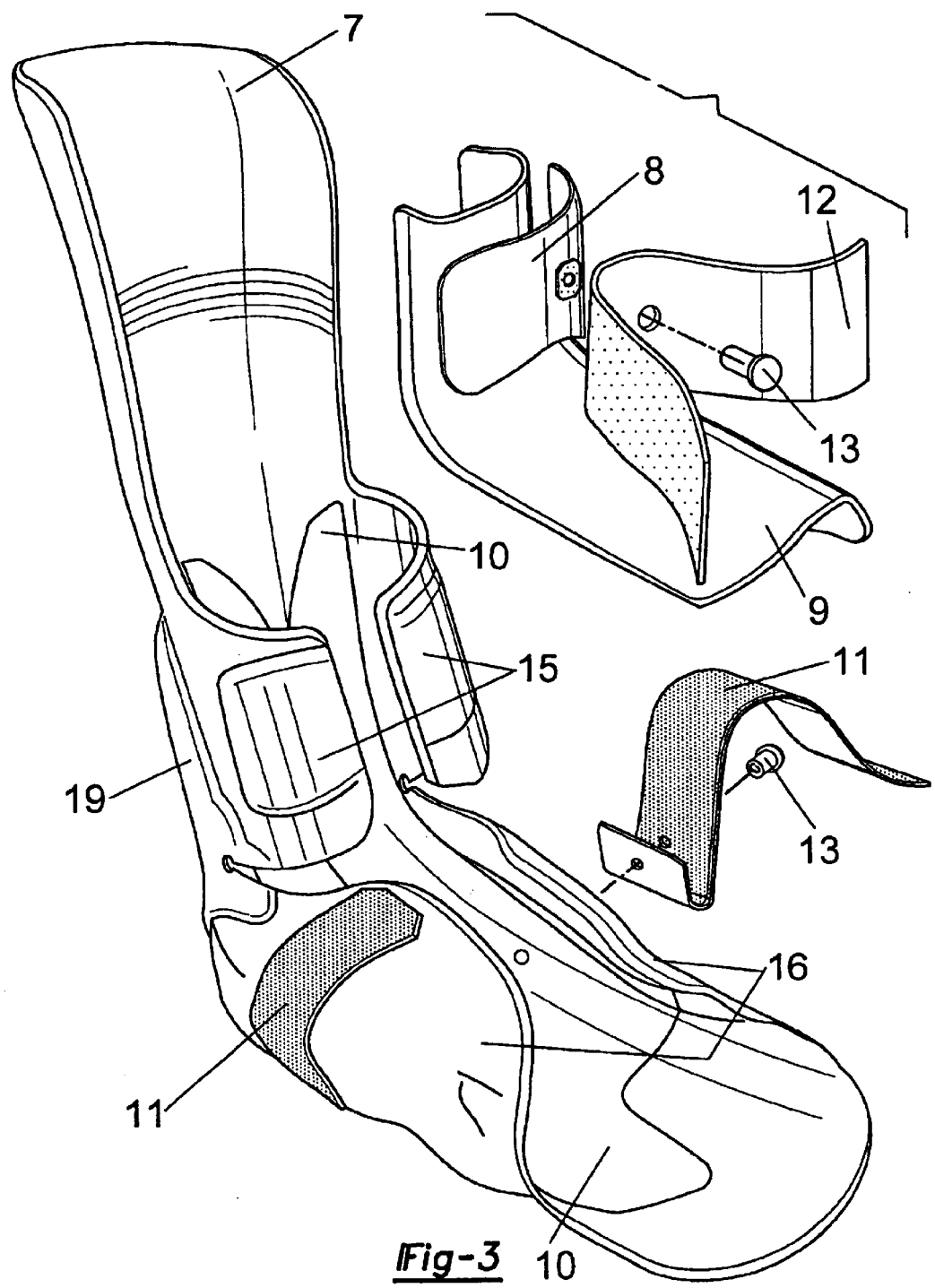
FIG. 3 is an exploded assembled view of the D-DAFO orthosis also showing the posterior shell (7), an outer anterior pre-tibial shell (8), tongue (9), liner (10), reinforcement (19), Velcro strap (11), elastic strap (12), attachment fasteners (13), and flanges (15) & (16).
Figure 4:
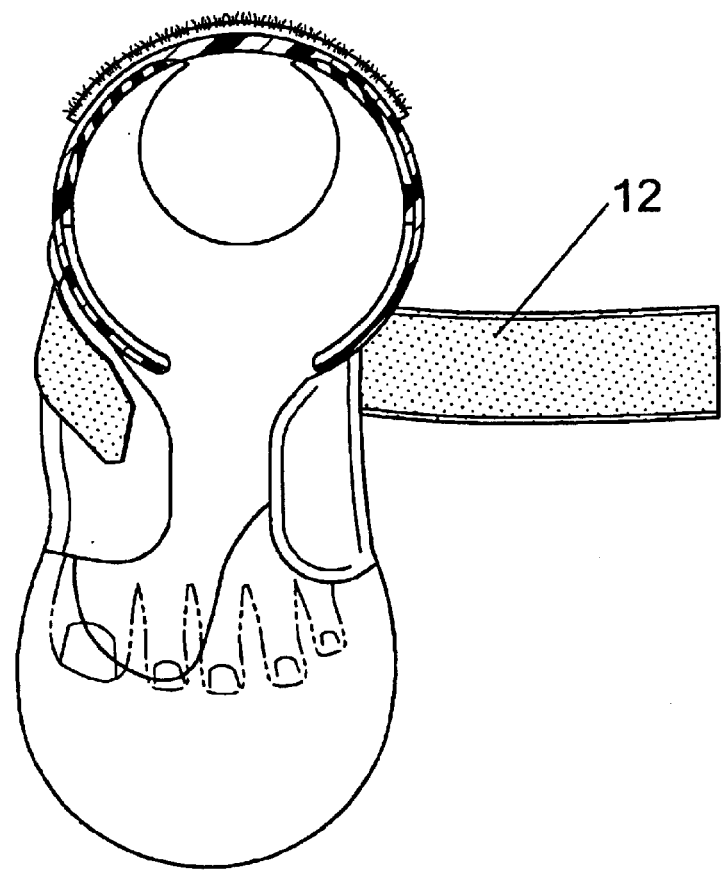
FIGS. 4 & 5 show a plan view representation of the D-DAFO with the Velco strap (11), and elastic strap (12) with a cross-section of the inner linings of the orthosis posterior and pre-tibial shell.
Figure 5:
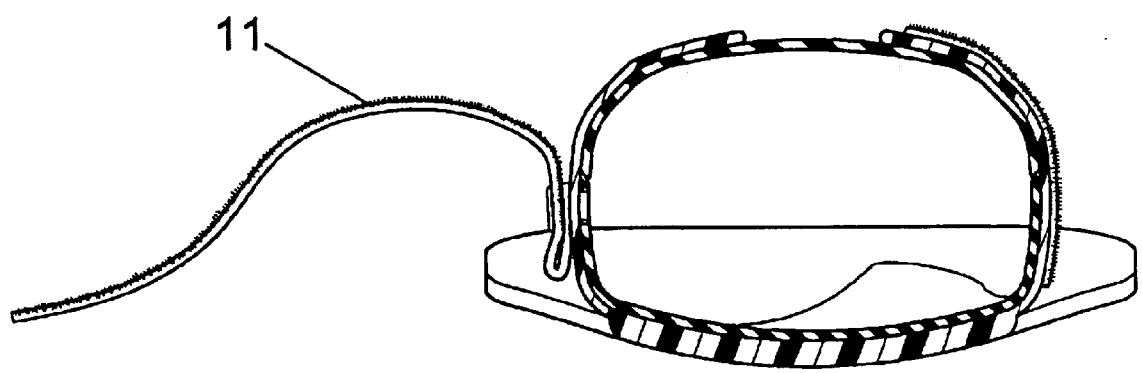

The D-DAFO (DeRoos-Dynamic Ankle Foot Orthosis) as generally represented in the subject invention and further defined by the preferred embodiment in FIGS. 1, 3 and comprises a posterior base shell (7), an outer anterior (pre-tibial ) shell (8) having an inside surface and an outside surface, the inside surface of the outer anterior pre-tibial shell is attached to an outside surface of an upper portion of a tongue (9), tongue (9) is adapted to cover an anterior portion at a lower leg and adopted to cover a top portion of a foot of a wearer, a liner (10), Velcro strap (11), an elastic Velcro strap (12), and attachment fasteners (13).

The posterior shell (7) is composed of TPE or similar polymer of nature providing a flexible yet stable shape. TPE is the most desirable with its blend of rubber and polyethylene plastic, giving it rigidity without brittleness. The posterior shell (7) is open on the front vertically and horizontally. The horizontal opening proceeds to the ankle axis in a wedge shape to allow for dorsiflexion and to allow the tibia to rotate. The vertical openings allow for donning and doffing. These openings of the posterior shell (7) create two pairs of upper and lower expernal flanges (15) and (16). The flanges (15) and (16) are flexible yet hold their shape to allow the proximal (upper) half of the tongue (9) and pre-tibial shell (8) to go forward pushing the upper (proximal) flanges ( 15) open. The pre-tibial shell (8) and tongue (9) is prevented from going out of the base shell by the flanges (15) and (16) memory and the elastic proximal (upper) strap (12). The pre-tibial shell (3) is prefered to be formed from Kydex.

The posterior base shell (7) includes an upper tibia portion with a front and back portion disposed about a vertical axis, and a lower ankle forefoot portion with a top and bottom portion disposed about a horzontal axis of patient's foot.

The posterior base shell (7) further includes a forefoot posting (17) and a hindfoot posting (13) at the bottom of the posterior base shell (7) for stability.

The thickness of the plastic TPE creates the resistance force on the pre-tibial shell (8) with the aid of the elastic Velcro strap (11). The thickness is determined by the size and weight of the patient. The Velcro strap (11) may be tightened to increase or decrease the support at the ankle and tibia. The tongue (9) and pre-tibial shell (8) provide a unique forward and backward movement. This movement of the top half of the tongue (9) (at the ankle axis) and pretibial shell (8) create the foundation of the D-DAFO's uniqueness giving it "dynamic stability." These dynamics allow the patient's tibia to rotate forward (anteriorly) and yet supported. The D-DAFO continuously provides the support to hold the patient in STN (sub-talar neutral) while simultaneously maintaining tone and exension synergy.

The upper flanges (15) have an inside surface and an outside surface, said upper flanges (15) extending forwardly from a lower tibia portion of the posterior base shell (7) and adapted for covering and supporting the ankle area of a wearer, wherein when said orthosis is worn by a wearer, the outside surface of the outer anterior shell (8) is positioned to contact directly with the inside surface of the upper flanges (15), and the elastic strap (12) is positioned to cover the outside surface of the upper flanges (15).

Other modifications not explicitly mentioned herein are also possible and within the scope of the present invention. It is the following claims, including all equivalents, which define the scope of the present invention.

What is claimed is:

1. A dynamic ankle foot orthosis comprising a posterior base shell with an upper tibia portion and a lower tibia portion, a tongue having an upper portion adapted to cover an anterior portion of a lower leg and lower portion adapted to cover a top portion of a foot of a wearer, a front portion and a back portion disposed about a vertical axis, and outer anterior pre-tibial shell having an inside surface and an outside surface, said inside surface is attached to an outside surface of the upper portion of said tongue, strap means attached to the outside surface of the outer anterior pre-tibial shell for securing said posterior base shell, said outer anterior pre-tibial shell and said tongue to a wearer; said posterior base shell further includes a lower ankle forefoot portion with a top and bottom portion disposed about a horizontal axis of a subject patient's foot, and a pair of upper flanges having an inside surface and an outside surface, said upper flanges extending forwardly from the lower tibia portion of the posterior base shell and adapted for covering and supporting the ankle area of the wearer, and wherein when said orthosis is worn by a wearer, the outside surface of the outer anterior pre-tibial shell is positioned to contact directly with the inside surface of said upper flanges, and said strap is positioned to cover the outside surface of said upper flanges.

2. A dynamic ankle orthosis according to claim 1, wherein said posterior base shell further includes a pair of lower flanges, and attachment means for securing another strap means to the lower flanges.

3. A dynamic ankle foot orthosis according to claim 1, including attachment means for securing said upper flanges of said posterior base shell to said strap means, and for securng a lower pair of flanges of said posterior base shell to another strap means.

4. A dynamic ankle foot orthosis according to claim 1, wherein said posterior base shell further includes forefoot posting and hind foot posting disposed about said bottom portion of said lower ankle forefoot portion.

5. A dynamic ankle foot orthosis comprising:

(a) a posterior base shell with an upper tibia portion and a lower tibia portion, a front portion and a back portion disposed about a vertical axis, a lower portion having a top portion and a bottom portion disposed about a generally horizontal axis, and a tongue having an upper portion adapted to cover an anterior portion of a lower leg and a lower portion adapted to cover a top portion of a foot of a wearer;

(b) said posterior base shell further includes a forefoot posting and a hind foot posting at the bottom portion of said lower portion of said posterior base shell;

(c) an outer anterior pre-tibial shell having an inside surface and an outside surface, said inside surface is attached to an outside surface of the upper portion of said tongue for engaging said posterior base shell about the vertical axis so as to maintain the ankle foot orthosis in proper attitude while enuring dynamic flexibility;

(d) said tongue disposed between the posterior base shell and the outer anterior pre-tibial shell;

(e) said front portion of said lower tibia portion of said posterior base shell further includes a pair of upper flanges having an inside surface and an outside surface, said upper flanges extending forwardly from the lower tibia portion of the posterior base shell and adapted for covering and supporting the ankle area of a wearer, said top portion of said lower portion of said posterior base shell further includes a pair of lower flanges;

(f) an upper strap attached to the outside surface of said outer anterior pre-tibial shell for retaining said posterior base shell, said outer anterior pre-tibial shell, and said upper portion of said tongue together, wherein when said orthosis is worn by a wearer, the outside surface of the anterior pre-tibial shell is positioned to contact directly with the inside surface of said upper flanges, and said upper strap is positioned to cover the outside surface of said upper flanges;

(g) a strap for retaining and securing the lower flanges of the lower portion of said posterior base shell to the lower portion of the tongue;

(h) a liner disposed on the top portion of said lower portion of said posterior base shell; and (i) fastener means provided for attaching and securing said upper strap and said strap to the pair of upper and lower flanges disposed upon the lower tibia portion and lower portion of said posterior base shell.

* * * * *

UNITED STATES PATENT AND TRADEMARK OFFICE
CERTIFICATE OF CORRECTION

PATENT NO.      : 6,860,864 B2                                        Page 1 of 1
DATED           : March 1, 2005
INVENTOR(S)     : Grant C. Meyer It is certified that error appears in the above-identified patent and that said Letters Patent is hereby corrected as shown below:

<u>Title page, Item [54] and Column 1, line 1,</u>
Title, "D-DAFO (DEROSS-DYNAMIC ANKLE FOOT ORTHOSIS)" should be
-- D-DAFO (DEROOS-DYNAMIC ANKLE FOOT ORTHOSIS) --.

Signed and Sealed this

First Day of November, 2005

JON W. DUDAS
*Director of the United States Patent and Trademark Office*